United States Patent
Maser et al.

(10) Patent No.: US 7,359,742 B2
(45) Date of Patent: Apr. 15, 2008

(54) SENSOR ASSEMBLY

(75) Inventors: Douglas R. Maser, Rogers, MN (US); Timothy L. Johnson, Plymouth, MN (US); Philip O. Isaacson, Chanhassen, MN (US)

(73) Assignee: Nonin Medical, Inc., Plymouth, MN (US)

( * ) Notice: Subject to any disclaimer, the term of this patent is extended or adjusted under 35 U.S.C. 154(b) by 309 days.

(21) Appl. No.: 10/988,040

(22) Filed: Nov. 12, 2004

(65) Prior Publication Data

US 2006/0106294 A1 May 18, 2006

(51) Int. Cl.
*A61B 5/00* (2006.01)

(52) U.S. Cl. ........................ 600/344; 600/340
(58) Field of Classification Search ................ 600/310, 600/322, 323, 340, 344
See application file for complete search history.

(56) References Cited

U.S. PATENT DOCUMENTS

| | | | |
|---|---|---|---|
| 4,167,331 A | 9/1979 | Nielsen | |
| 4,723,554 A * | 2/1988 | Oman et al. | 600/310 |
| 4,825,872 A | 5/1989 | Tan et al. | |
| 4,942,877 A | 7/1990 | Sakai et al. | |
| RE33,643 E | 7/1991 | Isaacson et al. | |
| 5,058,588 A | 10/1991 | Kaestle | |
| 5,267,562 A | 12/1993 | Ukawa et al. | |
| 5,285,783 A | 2/1994 | Secker | |
| 5,337,744 A | 8/1994 | Branigan | |
| 5,490,523 A | 2/1996 | Isaacson et al. | |
| 5,776,059 A * | 7/1998 | Kaestle et al. | 600/340 |
| 5,800,349 A | 9/1998 | Isaacson et al. | |
| 5,807,247 A | 9/1998 | Merchant et al. | |
| 5,846,190 A | 12/1998 | Woehrle | |
| 5,891,021 A | 4/1999 | Dillon et al. | |
| 6,018,673 A | 1/2000 | Chin et al. | |
| 6,298,255 B1 | 10/2001 | Cordero et al. | |
| 6,397,091 B2 | 5/2002 | Diab et al. | |
| 6,591,123 B2 | 7/2003 | Fein et al. | |
| 6,600,940 B1 | 7/2003 | Fein et al. | |
| 6,628,975 B1 | 9/2003 | Fein et al. | |
| 6,708,049 B1 | 3/2004 | Berson et al. | |
| 6,760,610 B2 | 7/2004 | Tschupp et al. | |
| 6,801,797 B2 | 10/2004 | Mannheimer et al. | |
| 2003/0195402 A1 | 10/2003 | Fein et al. | |

OTHER PUBLICATIONS

Datasheet on Reusable SpO2 Sensors, Koninklijke Philips Electronics N.V., Nov. 2003.

* cited by examiner

*Primary Examiner*—Eric F Winakur
(74) *Attorney, Agent, or Firm*—Fulbright & Jaworski L.L.P.

(57) ABSTRACT

A flexible finger sensor having a finger entrance, a sensor holder at a distal end of the assembly, and a fenestrated region disposed between the finger entrance and the sensor holder. A displacement resistant finger sensor and method of use for reducing motion-related artifacts by mechanical isolation from external forces by providing a resilient sensor body having a digit entrance, a sensor holder, and a fenestrated region between the digit entrance and the sensor holder. The sensor holder maintains sensing elements relative to a user's finger, with said sensing elements being in communication with a monitoring device via a lead wire. The lead wire may extend at a lateral edge of the sensor body. A force to the lead wire may be applied so as to distort the fenestrated region without substantially disturbing the sensing elements relative to the finger surface.

25 Claims, 9 Drawing Sheets

SENSOR ASSEMBLY

FIELD OF THE INVENTION

The present invention relates generally to physiological sensors. More specifically, the present invention relates to a fingertip sensor adapted to improve sensor stability in order to minimize the occurrence of motion-induced artifacts within a physiologic signal.

BACKGROUND OF THE INVENTION

Non-invasive physiological monitoring is a common means for testing, detecting, and treating a physiological condition. Typically, non-invasive monitoring techniques such as pulse oximetry, electrocardiography (ECG), electroencephalography (EEG), and ultrasonic imaging, to name a few, require that a sensor be placed in direct contact with a patient undergoing the procedure.

Pulse oximetry involves the non-invasive monitoring of oxygen saturation level in blood-profused tissue indicative of certain vascular conditions. In practice, light is passed through a portion of a patient's body which contains arterial blood flow. An optical sensor is used to detect light which has passed through the body, and variations in the detected light at various wavelengths are then used to determined arterial oxygen saturation and/or pulse rates. Oxygen saturation may be calculated using some form of the classical absorption equation know as Beer's law.

Accurate measurement of oxygen saturation levels are predicated upon optical sensing in the presence of arterial blood flow. A finger provides a convenient access to a body part through which light will readily pass. Local vascular flow in a finger is dependent on several factors which affect the supply of blood. Blood flow may be affected by centrally mediated vasoconstriction, which must be alleviated by managing the perceived central causes. Peripheral constriction via external compression, however, can be induced by local causes. One such cause of local vasococompression is the pressure exerted by the sensor on the finger. Many currently available pulse oximetry finger sensors have a hard shell which has a high profile and is maintained on the finger by the action of a spring. Since excess pressure on the finger can dampen or eliminate the pulsation in the blood supply to the finger, these springs are intentionally relatively weak. The result of this compromise is that the spring-held sensors readily fall off the finger. It is desirable for a finger sensor to be retained on the finger with only slight pressure, while at the same time being immune to easy dislocation.

Non-disposable finger sensors typically utilize a clamp design for retaining the sensor on the finger. Such devices generally consist of a small spring-loaded clip which attaches to the finger tip in a manner similar to a common clothespin.

Many known non-disposable sensors are relatively bulky. The prior art sensors with their high profile exhibit a relatively high inertia of the housing relative to the finger. This results in a susceptibility to relative motion between the sensor and the finger as the finger is moved. This relative motion manifests itself as motion artifacts in the detected signal. It would be desirable for a finger sensor to be as light as possible so as to minimized relative inertial motion between the sensor and the finger.

Motion artifacts caused by displacement of the lead wire are especially problematic for oximetric sensors. Common oximetric finger sensors often locate the lead wire from the sensor over a central portion of a patient's finger. When the patient flexes or curls his finger, it is common for the lead wire to pull against the sensor causing the light elements to be displaced.

Consequently, there is a need in the art for a sensor assembly which is capable of mechanically isolating a sensor holder without the need to tightly secure the sensor to the patient.

SUMMARY OF THE INVENTION

The present invention is directed to a sensor assembly which provides improved mechanical isolation between the sensor holder region and other regions of the sensor assembly. In one embodiment, the sensor assembly includes a collar, a fenestrated region, a sensor holder, and a sensor. The collar, the fenestrated region, and the sensor holder are preferably made of a flexible material, such as a polymer. The sensor can include any known sensors used for monitoring of physiological parameters.

In one embodiment of the invention, the collar defines an entrance into the sensor assembly. In one embodiment, a strain relief extends generally perpendicularly to the collar and is located near a lateral side of the sensor assembly. The strain relief cooperates with the collar to define a pathway for a lead wire which connects the sensor to a physiological monitor.

In one embodiment, the fenestrated region includes a plurality of bridges separated by windows. The fenestrated region may additionally be of a reduced thickness compared to other portions of the sensor assembly. In another embodiment of the invention, the fenestrated region can include one relatively large opening in the sensor assembly. The fenestrated region may respond to external forces transferred through the collar by substantial deformation, including stretching, twisting, buckling and bending. As a result, the fenestrated region contributes to mechanical isolation of the sensor holder from the collar. Consequently, when a force is applied to the collar, the relatively thin fenestrated region is able to stretch or distort without disrupting the sensor holder. The fenestrated region which can include one or more fenestrations or openings into the interior of the sensor assembly, promotes an increase in user comfortability and digit ventilation. The fenestrated region is optional and embodiments of the present invention may be device of one or more fenestrations.

In one embodiment, the sensor holder provides seats wherein portions of the sensor element is received. The seats are positioned such that the sensor element is optimally located with respect to the patient. A finger stop and guide may be provided within an interior of the finger assembly in order to facilitate the positioning of the finger relative to the sensor element.

In one embodiment, an elongated pleat extends across each lateral side of the sensor assembly. The pleats enable the sensor assembly to expand and accommodate a variety of finger sizes.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS AND FIGURES

For purposes of facilitating and understanding the subject matter sought to be protected, there is illustrated in the accompanying drawings an embodiment thereof. From an inspection of the drawings, when considered in connection with the following description, the subject matter sought to be protected, its construction and operation, and many of its advantages should be readily understood and appreciated.

Figure 10:
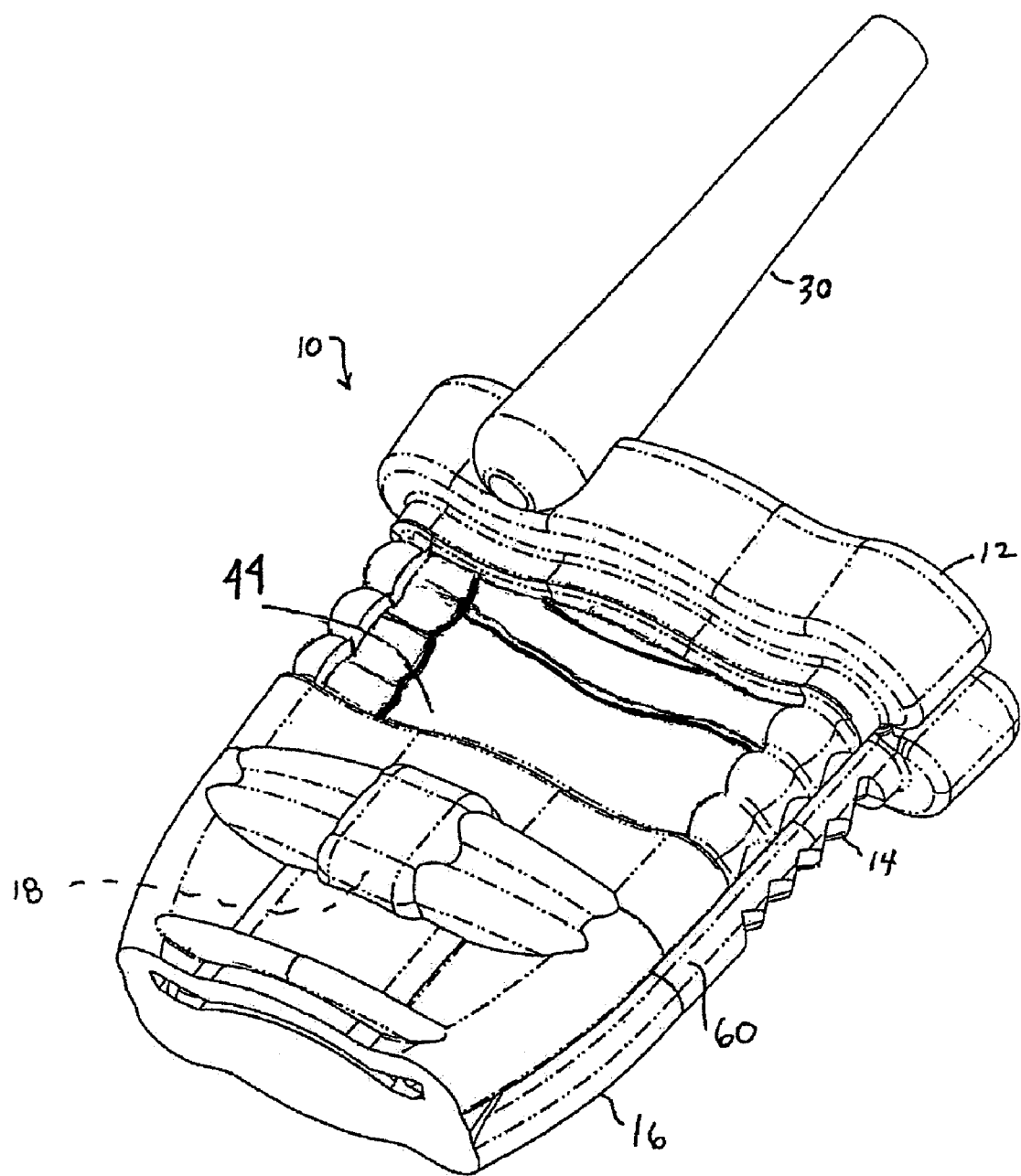

FIG. 10 a perspective view of another embodiment of the present invention.

Figure 11:
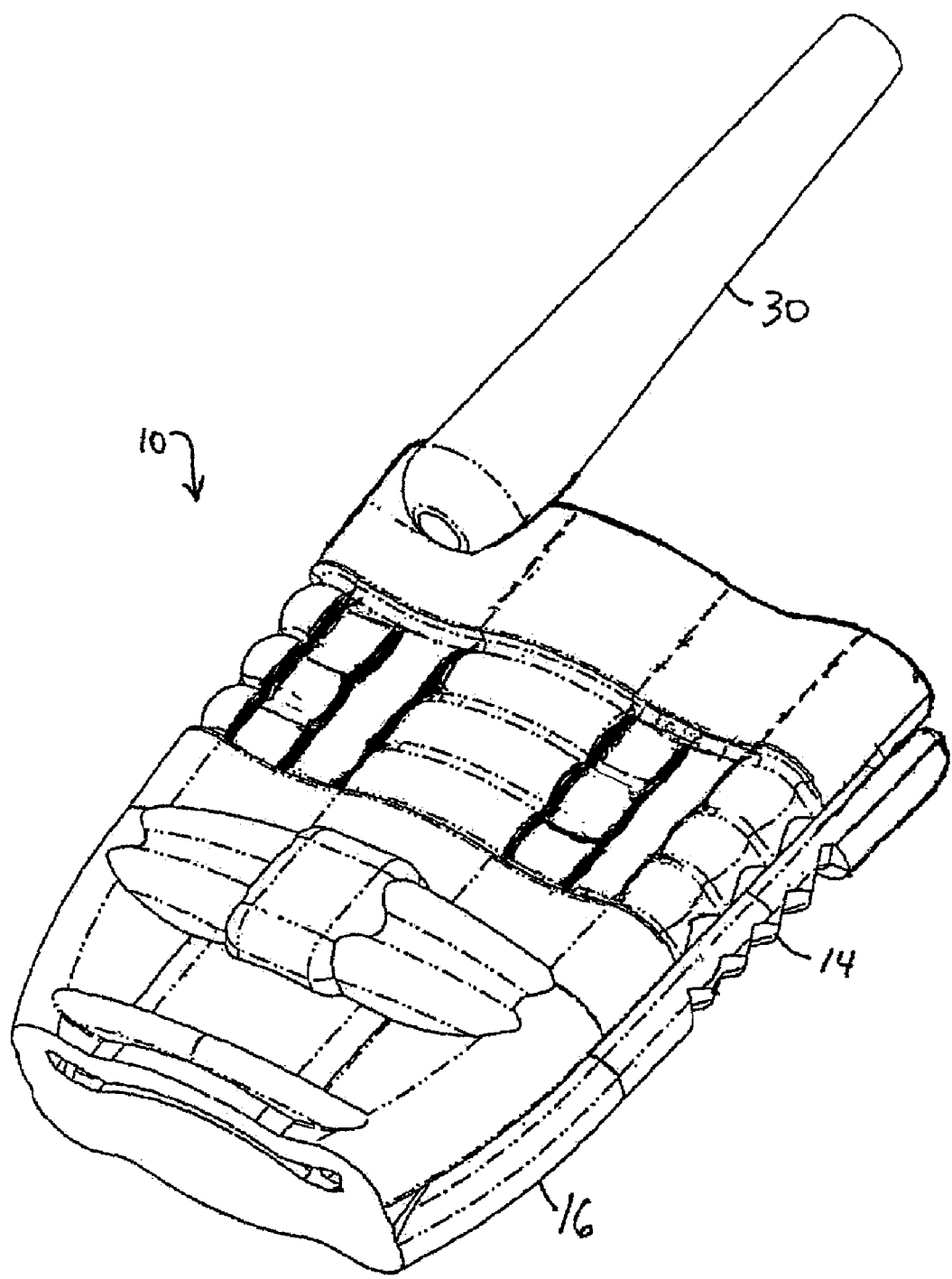

FIG. 11 is a perspective view of another embodiment of the present invention.

DETAILED DESCRIPTION OF THE PREFERRED EMBODIMENTS

In one embodiment of the present invention, as shown in FIGS. 1-6, a finger sensor assembly 10 is provided which mechanically isolates the sensor elements relative to other portions of the sensor assembly 10 in order to minimize inadvertent displacement of the sensor elements caused by external forces. For the purposes of explanation only, the present invention is disclosed utilizing an embodiment that is configured for the measurement of oxygen saturation through known oximetric transmittance techniques. As one skilled in the art can readily appreciate, the present invention is easily adaptable to accommodate a number of different physiological monitoring applications and configurations, including but not limited to, other optical sensors, reflective sensor, etc.

Figure 1:
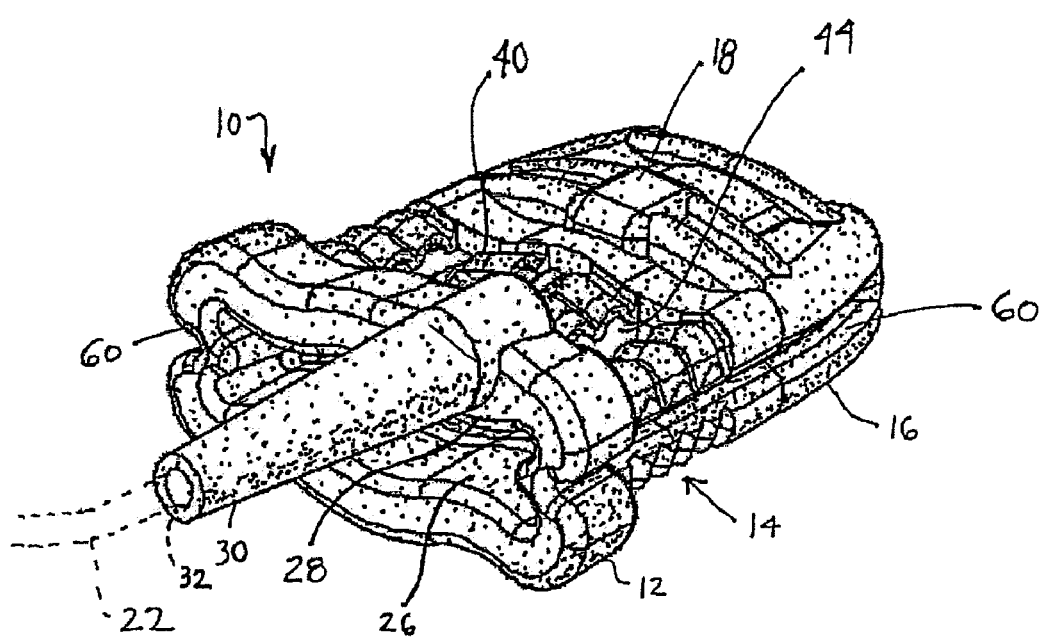
FIG. 1 is a perspective view of a first embodiment of a finger assembly according to the present invention.
Figure 2:
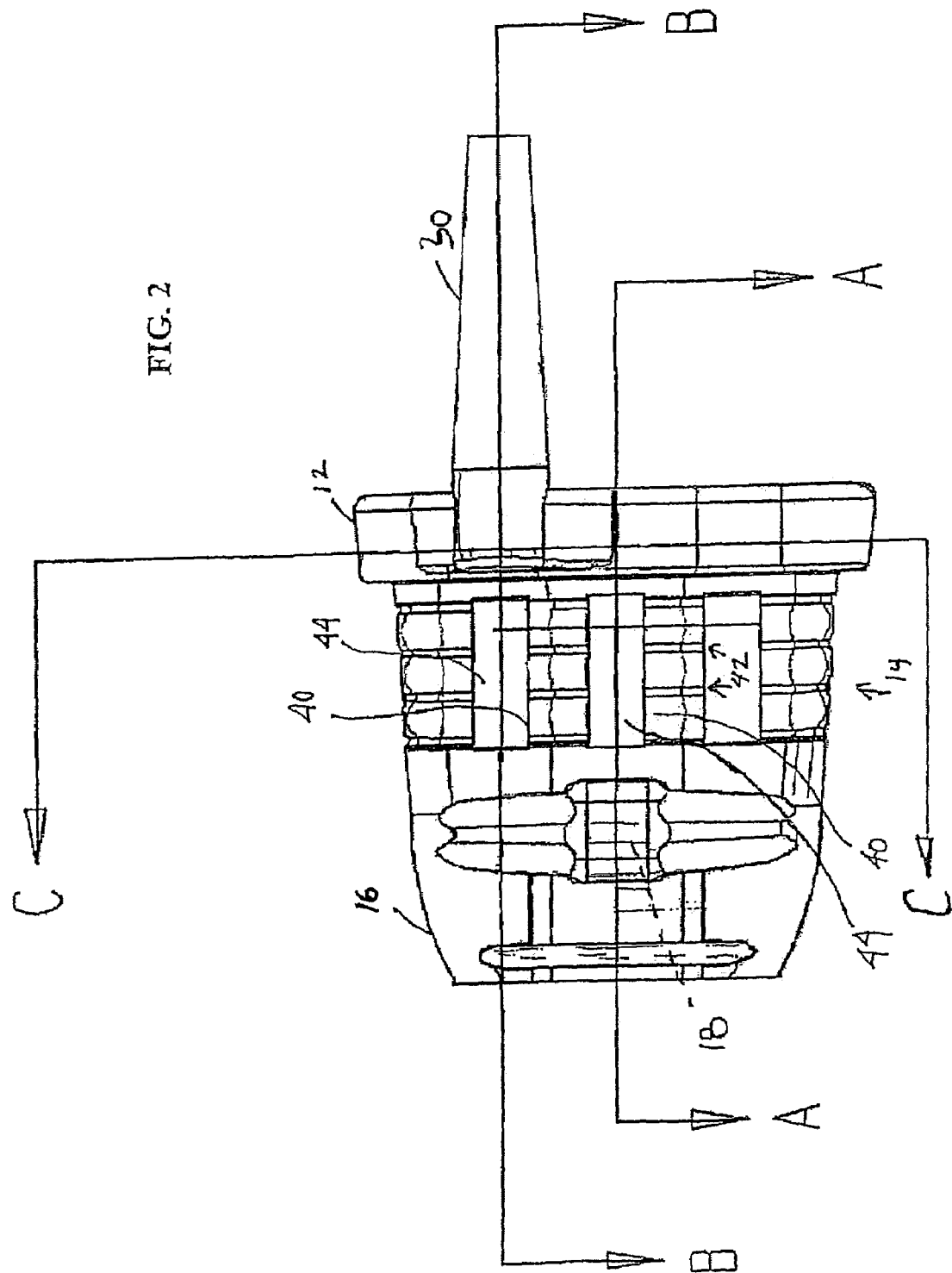
FIG. 2 is a top plan view of the finger assembly of FIG. 1.
Figure 4:
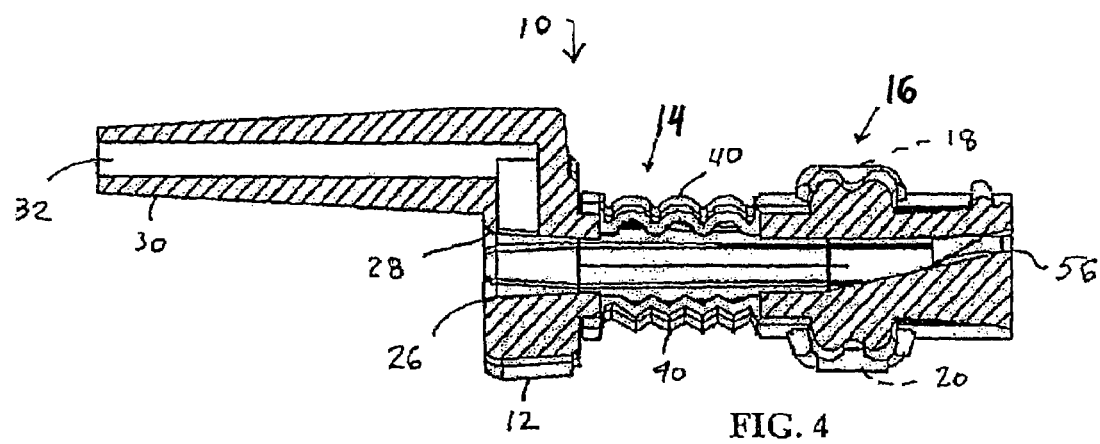
FIG. 4 is a cross-sectional view of the finger assembly of FIG. 2 taken along lines B-B.
Figure 5:
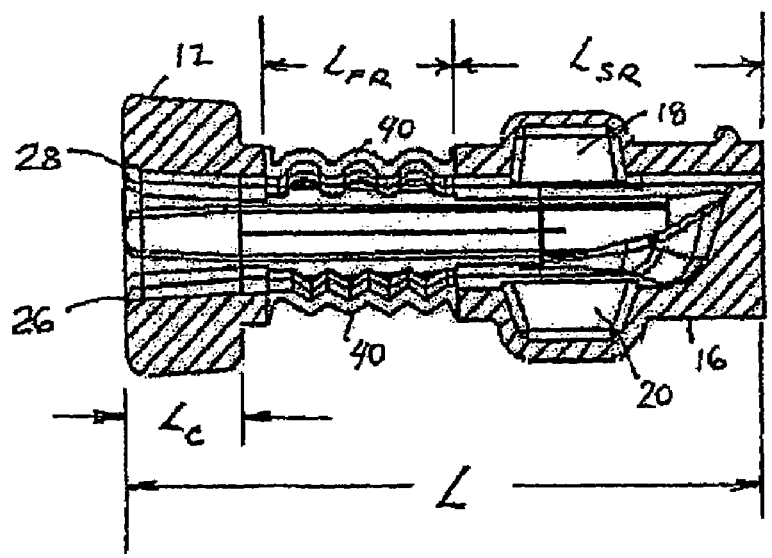
FIG. 5 is a cross-sectional view of the finger assembly of FIG. 2 taken along lines A-A.
Figure 6:
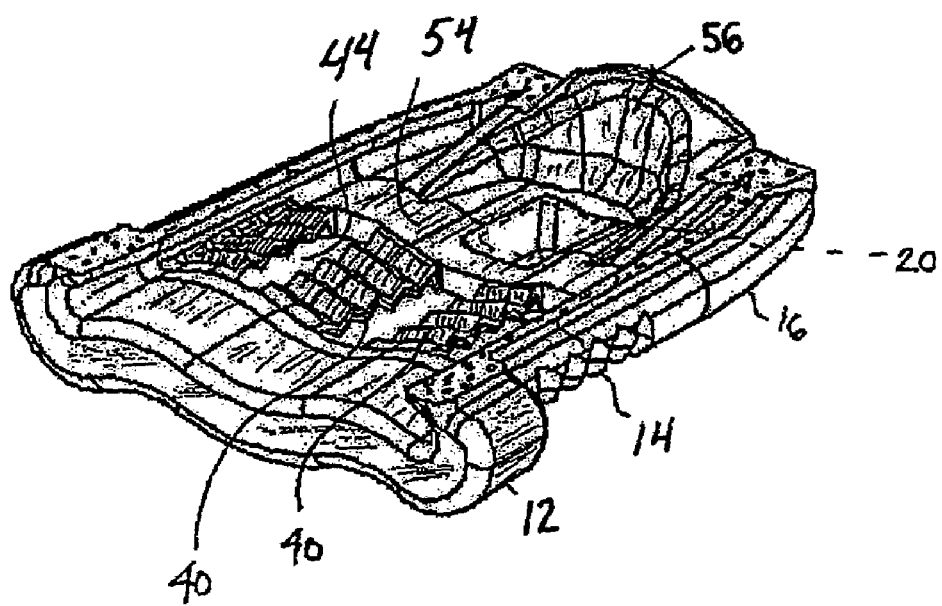
FIG. 6 is a cross-sectional view of the finger assembly of FIG. 2 taken along lines C-C.

FIG. 1 illustrates an embodiment of the assembly 10 adapted as an electro-optical sensor for a fingertip. In the illustrated embodiments, sensor assembly 10 is utilized within a system including a monitoring unit (not shown) for oxygen saturation measurement. Sensor assembly 10 preferably includes a molded polymeric body defining a collar 12, a fenestrated region 14, and sensor holder 16. As illustrated in FIG. 5, sensor assembly 10 further includes an oximetric sensor having one or more LED's 18 and one or more photodetectors 20 and being connected to the monitoring unit via a lead wire 22. The oximetric sensor can also or alternatively contain other known components utilized in the measurement of oxygen saturation.

Figure 3:
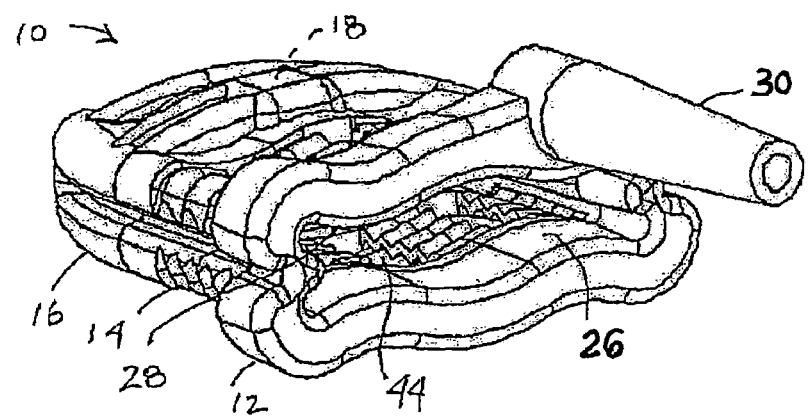
FIG. 3 is another perspective view of the finger assembly of FIG. 1

As shown in FIGS. 1 and 3, collar 12 defines an entrance into an interior of the sensor assembly 10. The collar 12 defines internal surfaces 26, 28 which are shaped to comfortably conform to the top and bottom surfaces of a human digit. The collar 12 is preferably substantially thicker than either the fenestrated region 14 or sensor holder 16. The molded shape and thickness of collar 12 enable it to comfortably engage the human digit. As illustrated in FIG. 5, collar 12 extends in a longitudinal direction and has a length $L_c$. The sensor assembly has an overall length, L.

The illustrated embodiment of sensor assembly 10 includes a strain relief 30 extending away from collar 12. The strain relief 30 defines an internal passageway 32 in communication with the interior of assembly 10. The strain relief 30 and collar 12 together define a pathway for a lead wire 22. In one preferred embodiment, the strain relief 30 is positioned near a lateral side of the collar 12. As described in more detail hereinafter, by so positioning the lead wire 22 near a lateral side of collar 12 the deleterious effects of external forces applied to lead wire 22 may be minimized. In the illustrated embodiment, strain relief 30 is positioned between the longitudinal centerline and the lateral edge of the sensor assembly 10. In other embodiments of the present invention, the strain relief 30 may be positioned further away from the centerline.

The fenestrated region 14 includes one or more fenestrations such as openings, windows, holes, perforations and/or slits. The fenestrations contribute to the mechanical isolation of the sensor holder 16 from the collar 12 by permitting the fenestrated region 14 to undergo substantial deformation or displacement relative to its relaxed state without displacing the sensor holder 16. In one embodiment, the fenestrated region 14 is preferably thinner than both the collar 12 and the sensor holder 16. As a result, the relatively thin fenestrated region 14 is able to deform in response to an external forces (transferred through collar 12 and/or sensor holder 16) while minimizing disturbances transferred to the sensor holder 16.

Figure 7:
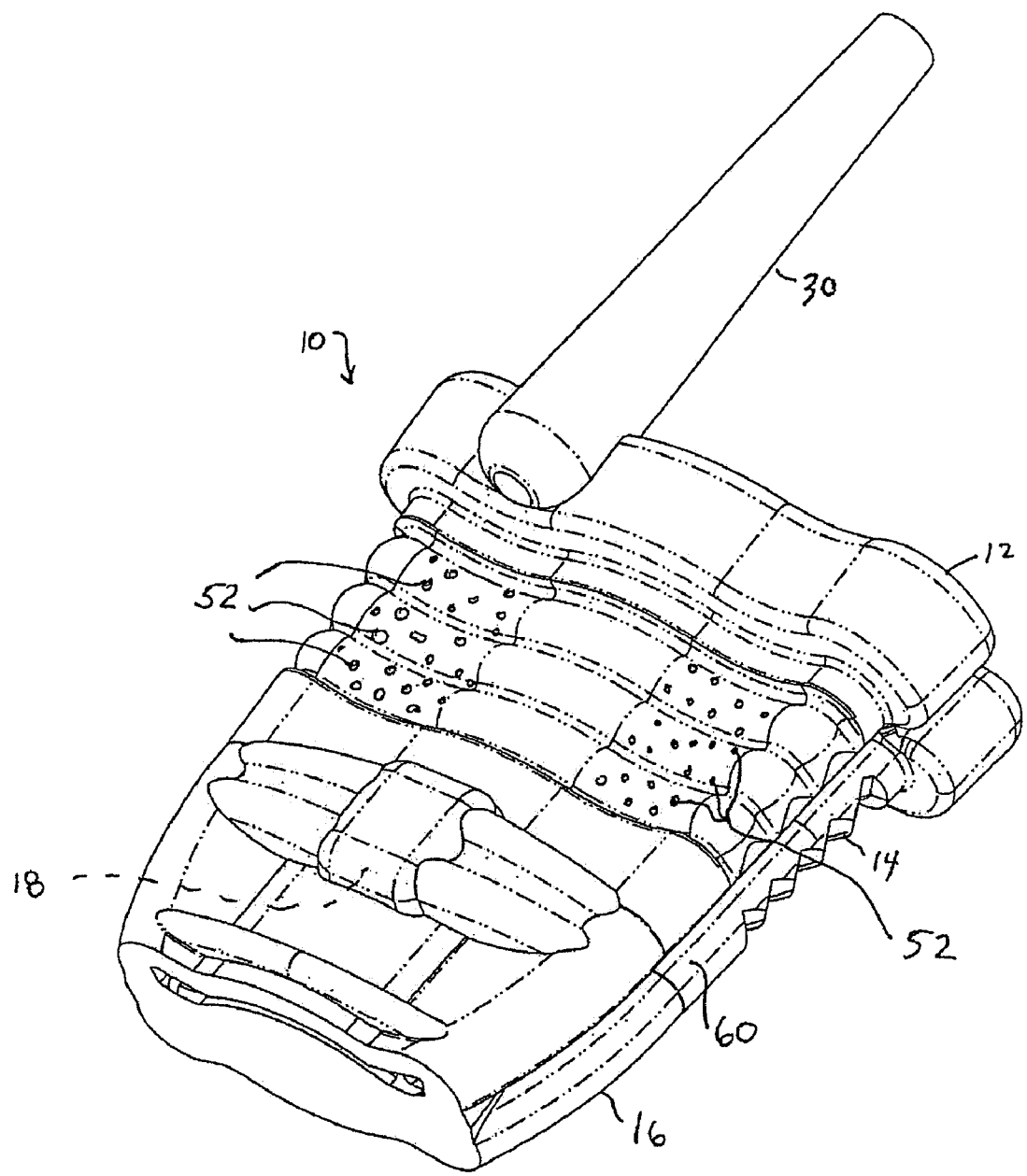
FIG. 7 is a perspective view of another embodiment of the present invention.
Figure 8:
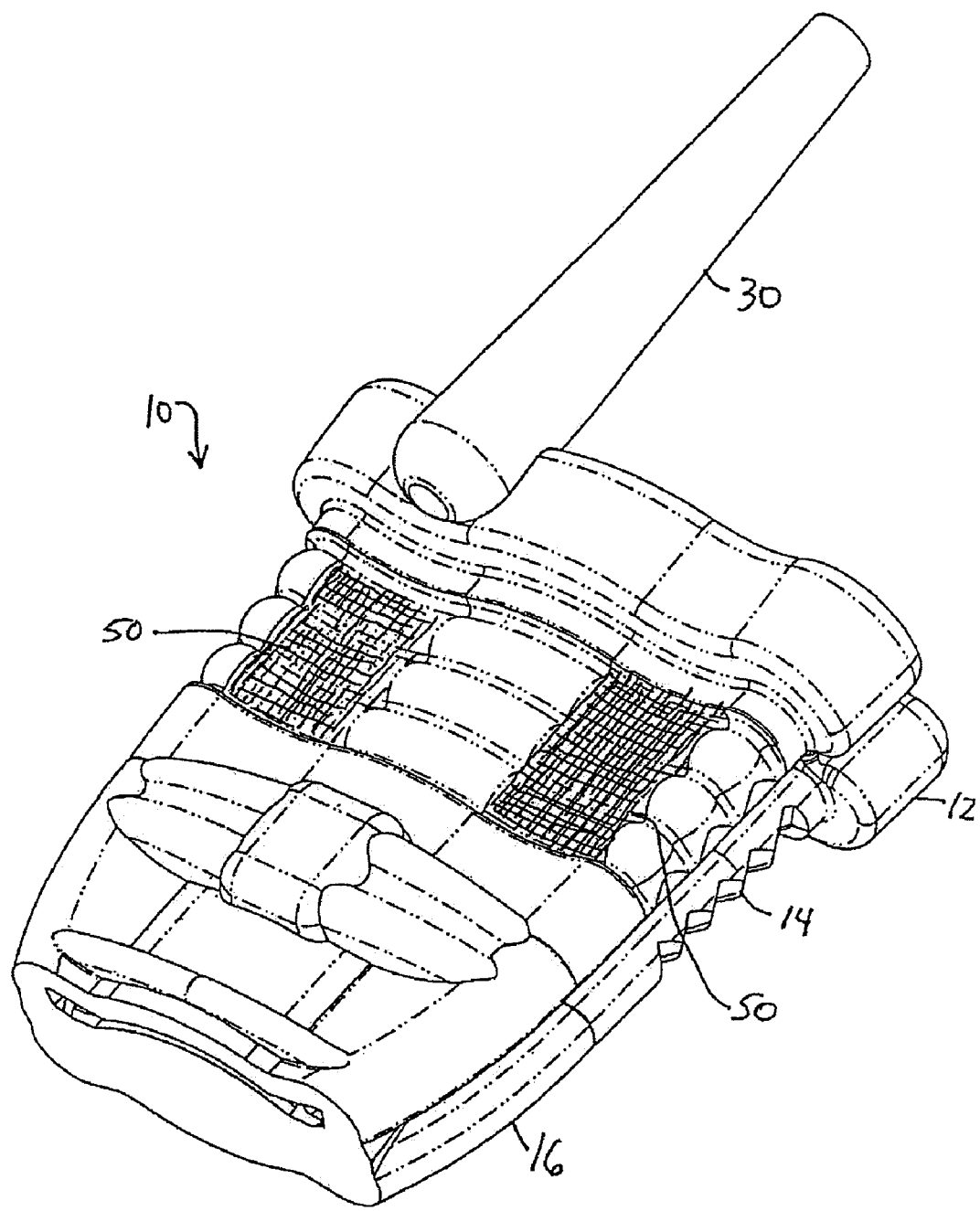
FIG. 8 is a perspective view of another embodiment of the present invention.
Figure 9:
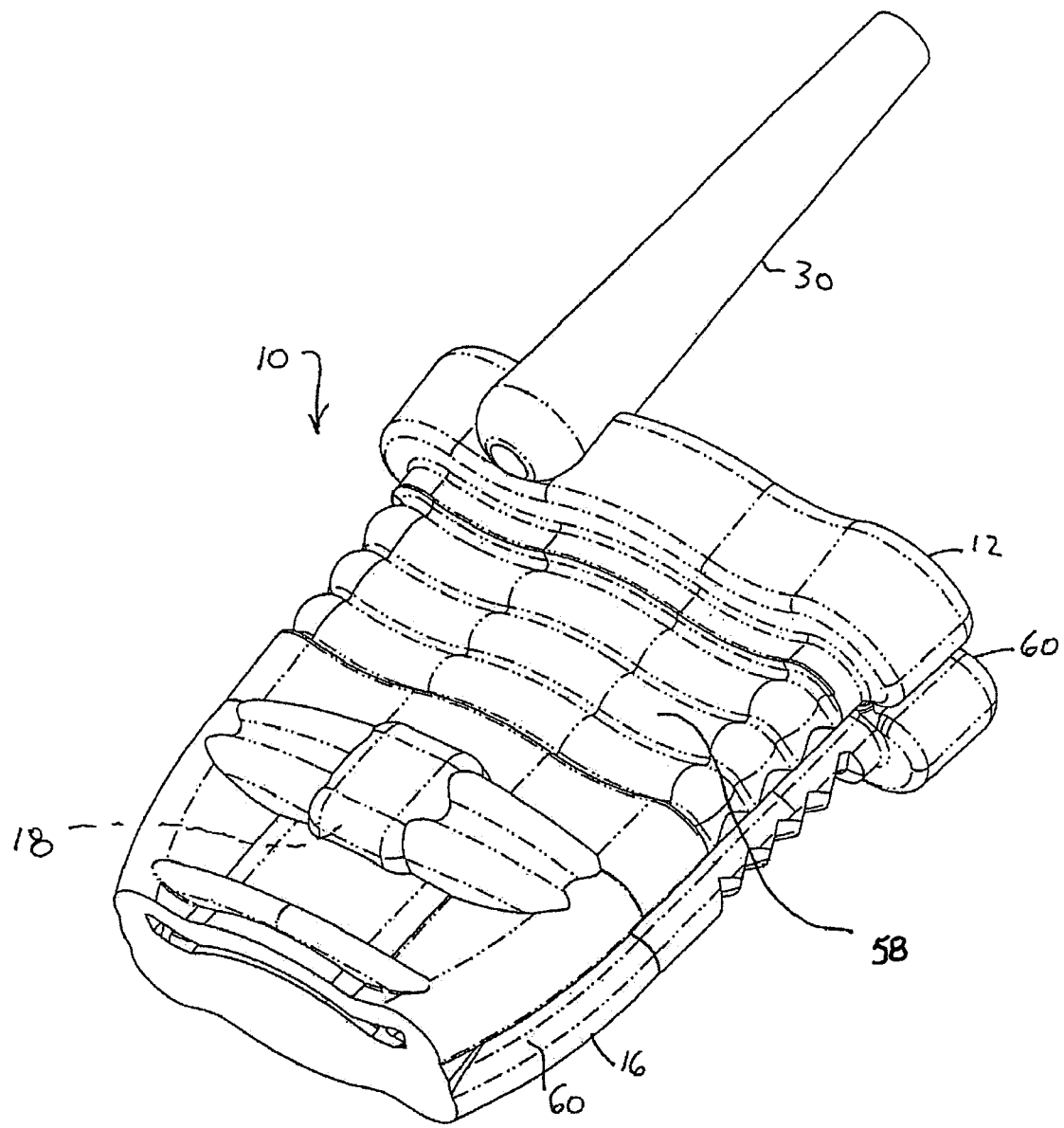
FIG. 9 is a perspective view of another embodiment of the present invention.

In the embodiment of FIGS. 1-6, the fenestrated region 14 includes a plurality of elongated bridges 40 which connect the collar 12 to the sensor holder 16. Each bridge 40 includes a plurality of resilient, laterally extending folds 42 which facilitate buckling or expansion of the bridges 40 in response to external forces transferred through lead wire 22. A plurality of openings 44 are defined between the bridges 40. As illustrated in FIG. 5, fenestrated region 14 extends in a longitudinal direction and has a length $L_{fr}$. Openings 44 of the illustrated embodiment are generally unobstructed. In other embodiments of the present invention, openings 44 may include a screen, mesh or fabric structure. For example, the fenestrations of the embodiment of FIG. 8 are defined by a screen element 50, and the embodiment of FIG. 7 includes a plurality of small holes 52 defining the fenestrations. FIG. 9 illustrates a finger sensor assembly 10 according to the present invention which lacks a fenestrated region. In place of the fenestrated region, an area of reduced thickness 58 is defined between the collar 12 and the sensor holder 16. As another alternative, FIG. 10 illustrates a finger assembly 10 having a single relatively large opening or fenestration 44 on each side.

Referring particularly to FIG. 5, preferably the length of the collar, $L_c$, is between 5% to 35% of the overall length of sensor assembly 10, L, and the length of the fenestrated region, $L_{fr}$, is between 20% to 50% of sensor 10 length, L. In a preferred embodiment, the length of the fenestrated region, $L_{fr}$, is approximately 35% of sensor length, L, and the collar length, $L_c$, is approximately 20% of sensor 10 length, L.

The sensor assembly 10 defines an expandable interior for receiving the user's finger. In the illustrated embodiments, the sensor assembly 10 includes a finger seat 54 and finger stop 56 for engaging the finger and thereby locating the sensor elements relative to the nail region of the user. The sensor holder 16 is adapted to align the sensor elements 18, 20 in position relative to a finger surface. Preferably, sensor holder 16 includes a finger seat 54 which functions to orient the sensor assembly 10 relative to a human digit so that sensor elements 18, 20 are optimally positioned relative to a finger surface. One skilled in the art will readily appreciate that the sensor holder 16 is easily reconfigured so that the seat 54 and/or stop 56 may be positioned or shaped to accommodate the needs of a particular sensor.

In the illustrated embodiments of the present invention, a pleat structure 60 extends along each opposing lateral side of the sensor assembly 10. The pleat structure 60 expands to allow the finger assembly 10 to accommodate a variety of differently sized fingers. Pleat structure 60 may include one or more folds of material. In other embodiments of the present invention (not shown), pleat structure 60 may be differently configured and/or limited to the collar 12 and/or sensor holder region 16.

Lead wire 22 may include one or more conductive wires or may include a light conducting fiber (not shown). In a preferred embodiment, a portion of lead wire 22 is maintained within the interior of the sensor assembly 10. That portion of the lead wire 22 within the sensor assembly 10 may be a conductive wire, a flexible conductive sheet, or another conductive element having a different configuration. Those of ordinary skill in the art will appreciate a variety of different ways to route portions of the lead wire 22 from the strain relief structure 30 to the sensor elements 18, 20 of the sensor holder 16.

Sensor assembly 10 may be comprised of thermoplastic materials, thermoelastic materials, silicone rubbers, etc. Sensor assembly 10 may be comprised of a plurality of different materials having different material properties. For example, collar 12 may be of a stiffer material than the material of fenestrated region 14 and/or sensor holder 16. One of ordinary skill in the art would appreciate a wide variety of different materials that may be utilized to practice the present invention.

Referring to FIG. 11, another embodiment of the sensor assembly 10 is illustrated. In this embodiment, collar 12 of sensor 10 is less massive than the embodiments of FIGS. 1.-10. Collar 12 of FIG. 11 may be comprised of a different material than other elements of sensor 10. For example, collar 12 may have a different durometer than other portions of sensor 10, but may otherwise be of an identical or similar material. As a result, collar 12 of the present invention need not be thicker than other portions of sensor 10. Collar 12 is defined as the structure proximate the digit opening of sensor 10.

In application, the digit is inserted into sensor assembly 10 and the lead wire 22 extends from the sensor assembly 10 and is connected to a physiological monitor. The sensor assembly 10 is maintained in place by resilient forces created by the collar 12, fenestrated region 14 and sensor holder 16. The strain relief 30 and collar 12 cooperate to oppose lateral movement of lead wire 22. Preferably, the fenestrated region 14 has a reduced capability to transfer forces applied at the collar to the sensor holder 16. In one embodiment of the present invention, the fenestrated region would be minimally capable of transferring a compressive force from the collar 12 to sensor holder 16, and would instead buckle or deform under such a compressive force. In a preferred embodiment, the strain relief 30 positions the lead wire 22 away from the center of the inserted finger. With this offset of lead wire 22 relative to the longitudinal axis of the sensor assembly 10, the patient is able to curl his finger without tensioning the lead wire 22 and disturbing the sensor holder 16.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, device, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A finger sensor assembly comprising:
a collar at a proximal end of the assembly;
a sensor holder at a distal end of the assembly;
a fenestrated region between the collar and the sensor holder; and
a non-fenestrated bridge extending between the collar and the sensor holder.

2. The finger sensor assembly of claim 1, wherein the sensor holder, fenestrated region, and collar define a resilient expandable interior volume which is adapted to receive a human digit.

3. The finger sensor assembly of claim 2, further comprising a finger stop adapted to position an end of the finger within the sensor holder.

4. The finger sensor assembly of claim 2, and further comprising a lead wire extending from the collar.

5. The finger sensor assembly of claim 4, and further comprising a strain relief extending from the collar and positioned near a lateral edge of the collar.

6. The finger sensor assembly of claim 1, wherein a thickness of material of the fenestrated region is thinner than material defining the collar and the sensor holder.

7. The finger sensor assembly of claim 1, wherein the sensor holder includes a pair of sensor seats linearly located on opposing sides of the sensor holder.

8. The finger sensor assembly of claim 1, wherein the sensor holder is adapted to position an oximetric sensor proximate to a distal end of a human digit.

9. A finger sensor assembly comprising:
a collar at a proximal end of the assembly;

a sensor holder at a distal end of the assembly;

a fenestrated region connecting the collar to the sensor holder; and a side pleat.

10. A finger sensor assembly comprising:

a resilient body adapted to be placed upon a user's finger tip, said resilient body defining an entrance into an interior region adapted to engage surfaces of the finger tip, and having a side pleat at a lateral edge thereof;

a sensor attached to the resilient body and having at least partial access into the interior region for sensing a physiologic parameter of the user;

a lead communicating a signal from the sensor to an external monitor; and a lead strain relief structure extending away from the resilient body and engaging a portion of the lead, wherein the strain relief structure is positioned near a lateral edge of the resilient body.

11. The finger sensor assembly of claim 10 wherein the lead strain relief structure is an elongated element having an internal passageway through which the portion of the conductive lead is routed.

12. The finger assembly of claim 10 wherein the lead strain relief structure is positioned proximate to the pleat.

13. A finger sensor assembly comprising:

a flexible body adapted to be resiliently secured upon a user's finger tip, said body defining an entrance into an interior at a proximal end and a sensor holder near a distal end, said sensor holder maintaining a physiologic sensor element in proximity to a finger surface of the user, said flexible body having a plurality of fenestrations adjacent to the entrance and disposed between the entrance and the sensor holder, said body having a plurality of bridges extending across at least some of the plurality of fenestrations, and said plurality of fenestrations limiting an amount of material between the entrance and the sensor holder.

14. The finger assembly of claim 13 wherein the plurality of fenestrations includes a mesh structure.

15. The finger assembly of claim 13 further comprising a collar at the entrance, said collar being of substantially thicker or stiffer material than material proximate the plurality of fenestrations.

16. The finger assembly of claim 15 wherein the plurality of fenestrations is defined between the collar and the sensor holder.

17. The finger assembly of claim 15 further comprising a laterally-offset lead wire strain relief structure.

18. A method of using a finger sensor to reduce motion-related artifacts by mechanical isolation from external forces comprising:

providing a resilient sensor body having a collar portion, a sensor holder, and boht a fenestrated region between the collar portion and the sensor holder and at least one non-fenestrated bridge between the collar and the sensor holder, said sensor holder maintaining sensing elements relative to a surface of a user's finger, said sensing elements being in communication with a monitoring device via a lead wire, said lead wire extending from the collar portion proximate to a lateral edge thereof; and applying a force to the lead wire so as to distort the collar portion and the fenestrated region without substantially disturbing the sensing elements relative to the finger surface.

19. A method of using a finger sensor to reduce motion-related artifacts by mechanical isolation from external forces comprising:

providing a resilient sensor body having a digit entrance, a sensor holder, and a fenestrated region adjacent to the digit entrance disposed between the digit entrance and the sensor holder, said sensor body having a side pleat, said sensor holder maintaining sensing elements relative to a surface of a user's finger, said sensing elements being in communication with a monitoring device via a lead wire, and said lead wire extending at a lateral edge proximate to the digit entrance of the sensor body; and applying a force to the lead wire so as to distort the fenestrated region without substantially disturbing the sensing elements relative to the finger surface.

20. A finger sensor assembly comprising:

a collar at a proximal end of the assembly;

a sensor holder at a distal end of the assembly;

a fenestrated region connecting the collar to the sensor holder; and a pleat structure extending along at least a portion of lateral portions of the sensor assembly proximate to the fenestrated region.

21. The finger sensor assembly of claim 20, wherein the sensor holder, fenestrated region, and collar define a resilient expandable interior volume which is adapted to receive a human digit.

22. The finger sensor assembly of claim 21, further comprising a finger stop adapted to position an end of the finger within the sensor holder.

23. The finger sensor assembly of claim 20, further comprising a strain relief extending from the collar and positioned near a lateral edge of the collar.

24. A finger sensor assembly comprising:

a collar at a proximal end of the assembly;

a sensor holder at a distal end of the assembly;

a fenestrated region connecting the collar to the sensor holder; and at least one elongated non-fenestrated bridge between the collar and the sensor holder, wherein the finger sensor assembly has an overall length, L, and the collar has a length, $L_c$, which is between 5% to 35% of L, and the fenestrated region has an overall length, $L_{fr}$, which is between 20% to 50% of L.

25. The finger sensor assembly of claim 24 wherein the length of the fenestrated region, $L_{fr}$, is approximately 35% of sensor length, L, and the collar length, $L_c$, is approximately 20% of sensor 10 length, L.

* * * * *